(12) United States Patent
Lischinsky et al.

(10) Patent No.: US 9,827,437 B2
(45) Date of Patent: Nov. 28, 2017

(54) SKIN TREATMENT DEVICES AND METHODS

(71) Applicant: EndyMed Medical Ltd., Caesarea (IL)

(72) Inventors: Daniel Lischinsky, Ramat Ishay (IL); Yoram Harth, Herzlia (IL)

(73) Assignee: ENDYMED MEDICAL LTD, Caesarea (IL)

( * ) Notice: Subject to any disclaimer, the term of this patent is extended or adjusted under 35 U.S.C. 154(b) by 335 days.

(21) Appl. No.: 14/220,315

(22) Filed: Mar. 20, 2014

(65) Prior Publication Data

US 2014/0207217 A1   Jul. 24, 2014

Related U.S. Application Data

(63) Continuation-in-part of application No. 13/922,254, filed on Jun. 20, 2013, which is a continuation-in-part
(Continued)

(51) Int. Cl.
*A61B 18/14* (2006.01)
*A61N 5/00* (2006.01)
(Continued)

(52) U.S. Cl.
CPC ............ *A61N 5/00* (2013.01); *A61B 18/1206* (2013.01); *A61B 18/14* (2013.01); *A61N 1/0476* (2013.01);
(Continued)

(58) Field of Classification Search
CPC ................ A61B 18/1206; A61B 18/14; A61B 2018/00452; A61B 2018/00458;
(Continued)

(56) References Cited

U.S. PATENT DOCUMENTS 5,334,193 A   8/1994   Nardella
5,383,917 A   1/1995   Desai et al.
(Continued)

FOREIGN PATENT DOCUMENTS

CN   202207398   5/2012
EP   2291223   3/2011
(Continued)

OTHER PUBLICATIONS

PCT Search Report dated Jul. 20, 2015 for PCT application PCT/IL2015/0502890.
(Continued)

*Primary Examiner* — Michael Peffley
(74) *Attorney, Agent, or Firm* — Pearl Cohen Zedek Latzer Baratz LLP

(57) ABSTRACT

Radiofrequency (RF) skin treatment devices and methods are provided herein. RF energy is delivered via electrodes in a phase-controlled manner which heats skin volumes below the surface more than the skin surface itself. At least one electrode at least partially encloses at least one other electrode. The combination of controlling the phases of the RF energy delivered to different electrodes and the enclosing configuration of the electrodes allows concentrating the delivered energy in specific regions below the skin surface at a particularly high efficiency. Configurations of the enclosing and the enclosed electrodes, their forms and combinations with other electrodes and the phase polarities applied to the electrodes are also provided.

18 Claims, 11 Drawing Sheets

Related U.S. Application Data of application No. 13/865,658, filed on Apr. 18, 2013, now abandoned, which is a continuation of application No. 12/802,518, filed on Jun. 7, 2010, now abandoned, which is a continuation-in-part of application No. 11/654,914, filed on Jan. 17, 2007, now Pat. No. 8,206,381.

(60) Provisional application No. 61/665,552, filed on Jun. 28, 2012, provisional application No. 61/213,409, filed on Jun. 5, 2009, provisional application No. 61/213,410, filed on Jun. 5, 2009, provisional application No. 60/759,289, filed on Jan. 17, 2006, provisional application No. 60/774,167, filed on Feb. 17, 2006.

(51) Int. Cl.

| | | |
|---|---|---|
| *A61B 18/12* | (2006.01) | |
| *A61N 1/32* | (2006.01) | |
| *A61N 1/04* | (2006.01) | |
| *A61N 1/36* | (2006.01) | |
| *A61N 7/00* | (2006.01) | |
| *A61B 18/00* | (2006.01) | |

(52) U.S. Cl.
CPC .......... *A61N 1/0492* (2013.01); *A61N 1/328* (2013.01); *A61N 1/36014* (2013.01); *A61B 2018/0075* (2013.01); *A61B 2018/00452* (2013.01); *A61B 2018/00476* (2013.01); *A61B 2018/00678* (2013.01); *A61B 2018/00702* (2013.01); *A61B 2018/00791* (2013.01); *A61B 2018/00869* (2013.01); *A61B 2018/00875* (2013.01); *A61B 2018/1273* (2013.01); *A61B 2018/1467* (2013.01); *A61N 7/00* (2013.01); *A61N 2007/0008* (2013.01)

(58) Field of Classification Search
CPC .. A61B 2018/00464; A61B 2018/0047; A61B 2018/00654; A61B 2018/00476; A61B 2018/00678; A61N 1/0476
See application file for complete search history.

(56) References Cited

U.S. PATENT DOCUMENTS

| | | | | |
|---|---|---|---|---|
| 5,462,545 A | * | 10/1995 | Wang | A61B 18/1492 600/373 |
| 5,620,481 A | | 4/1997 | Desai et al. | |
| 5,630,426 A | | 5/1997 | Eggers | |
| 5,755,753 A | * | 5/1998 | Knowlton | A61B 18/12 606/33 |
| 6,042,580 A | | 3/2000 | Simpson | |
| 6,059,778 A | | 5/2000 | Sherman | |
| 6,106,524 A | | 8/2000 | Eggers | |
| 6,139,569 A | | 10/2000 | Ingle | |
| 6,210,406 B1 | | 4/2001 | Webster | |
| 6,228,078 B1 | * | 5/2001 | Eggers | A61B 18/12 604/114 |
| 6,387,380 B1 | | 5/2002 | Knowlton | |
| 6,413,255 B1 | * | 7/2002 | Stern | A61B 18/14 606/41 |
| 6,786,906 B1 | | 9/2004 | Cobb | |
| 8,206,381 B2 | | 6/2012 | Lischinsky et al. | |
| 2001/0008967 A1 | | 7/2001 | Sherman | |
| 2002/0120261 A1 | | 8/2002 | Morris | |
| 2005/0222565 A1 | | 10/2005 | Manstein | |
| 2007/0088413 A1 | * | 4/2007 | Weber | A61B 18/14 607/99 |
| 2007/0293918 A1 | | 12/2007 | Abbott et al. | |
| 2008/0183251 A1 | * | 7/2008 | Azar | A61B 18/18 607/101 |
| 2008/0312651 A1 | | 12/2008 | Pope et al. | |
| 2011/0015625 A1 | * | 1/2011 | Adanny | A61B 18/1233 606/33 |
| 2011/0245735 A1 | | 10/2011 | Eckhouse et al. | |
| 2013/0282085 A1 | | 10/2013 | Lischinsky et al. | |
| 2013/0289679 A1 | | 10/2013 | Eckhouse et al. | |

FOREIGN PATENT DOCUMENTS

| | | |
|---|---|---|
| JP | 2011-004882 | 1/2011 |
| KR | 101065611 | 9/2011 |
| WO | WO 2007/046886 | 4/2007 |
| WO | WO 2009/126117 | 10/2009 |
| WO | WO 2012/052986 | 4/2012 |

OTHER PUBLICATIONS

GB Search Report dated Jan. 19, 2015 for GB application 1410954.0.
Office Action dated Dec. 10, 2015 for U.S. Appl. No. 13/922,254.
Final Office Action dated Jun. 3, 2016 for U.S. Appl. No. 13/922,254.
Office Action dated Nov. 4, 2016 for U.S. Appl. No. 13/922,254.
Office Action dated Feb. 2, 2012 for U.S. Appl. No. 12/802,518.
Office Action dated Oct. 18, 2012 for U.S. Appl. No. 12/802,518.
Office Action dated Nov. 2, 2015 for U.S. Appl. No. 13/885,658.
European Search Report dated Oct. 9, 2017 for corresponding European Application 15764373.5 filed Mar. 19, 2015.

* cited by examiner

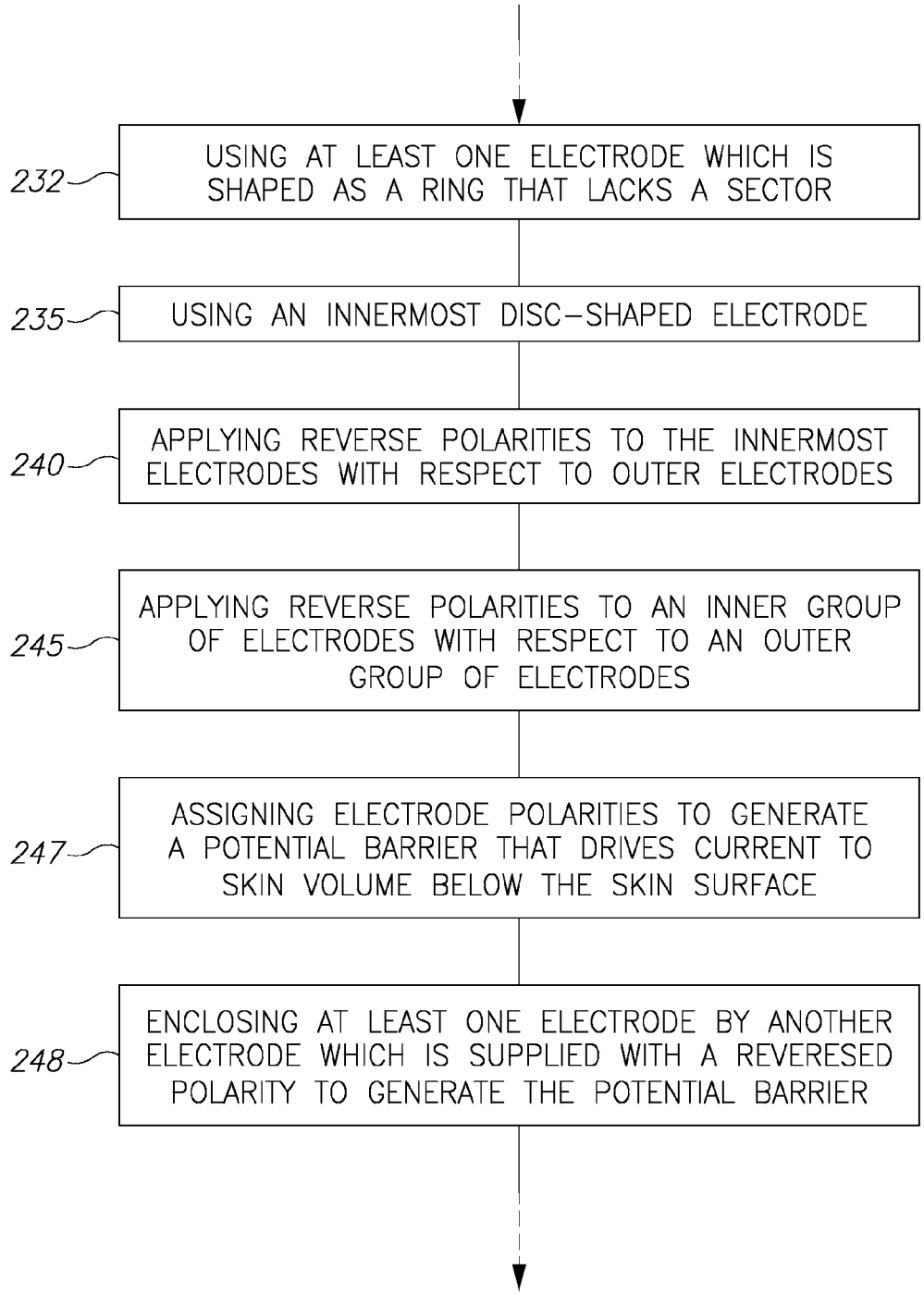
Figure 6 (cont. 1)

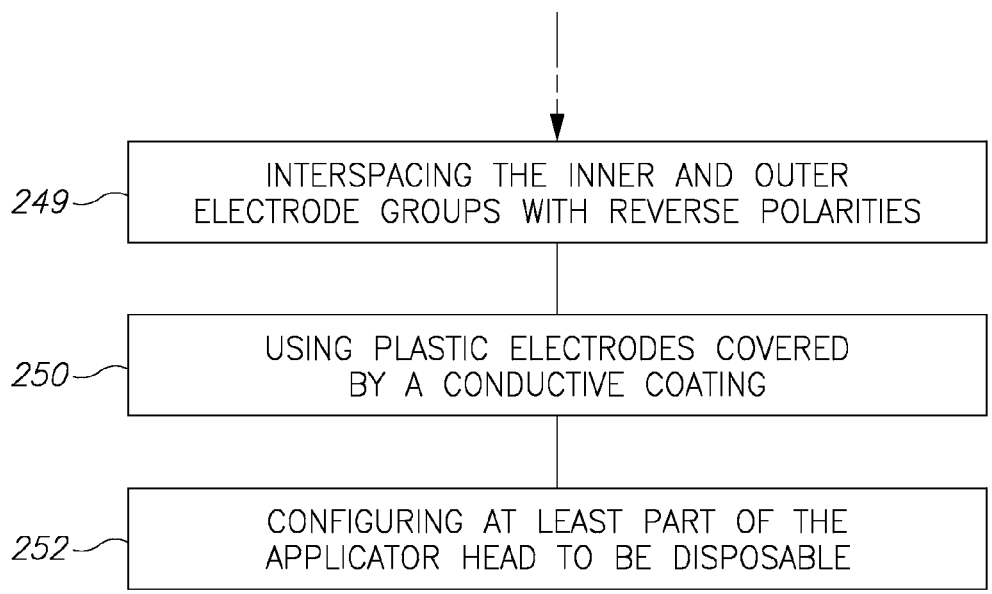
Figure 6 (cont. 2)

SKIN TREATMENT DEVICES AND METHODS

CROSS REFERENCE TO RELATED APPLICATIONS

This application is a continuation in part of U.S. patent application Ser. No. 13/922,254, filed on Jun. 20, 2013, which claims the benefit of U.S. Provisional Patent Application No. 61/665,552, filed on Jun. 28, 2012, and also is a continuation in part of U.S. patent application Ser. No. 13/865,658, filed on Apr. 18, 2013, which is a continuation of U.S. patent application Ser. No. 12/802,518, filed on Jun. 7, 2010, now abandoned, which claims priority under 35 U.S.C. §119 to U.S. Provisional Patent Application No. 61/213,409, filed Jun. 5, 2009, and U.S. Provisional Patent Application No. 61/213,410, filed Jun. 5, 2009. U.S. patent application Ser. No. 12/802,518 is also a continuation-in-part application of U.S. patent application Ser. No. 11/654,914, filed Jan. 17, 2007, now U.S. Pat. No. 8,206,381, which claims priority under 35 U.S.C. §119 to U.S. Provisional Patent Application No. 60/759,289, filed Jan. 17, 2006, and U.S. Provisional Patent Application No. 60/774,167, filed Feb. 17, 2006. Each such noted application is herein incorporated by reference in its entirety.

BACKGROUND OF THE INVENTION

1. Technical Field

The present invention relates to the field of skin treatment, and more particularly, to radiofrequency (RF) skin treatment.

2. Discussion of Related Art

Energy emitting devices are typically used to heat cutaneous or subcutaneous tissues or to trigger a non-thermal chemical or photochemical reaction. In many cases, heating of the epidermis should be limited to prevent skin burns. This in turn limits the amount of energy that is delivered to deeper tissues. In a professional clinic setting, energy emitting skin treatment devices use skin cooling to prevent over heating of the epidermis. Due to the high cost and the size of a device which incorporates such functionality, active cooling is not practical in consumer, home-use devices.

U.S. Pat. No. 8,206,381, which is incorporated herein by reference in its entirety, discloses an electrosurgical device for applying phase controlled RF energy to a treatment site.

SUMMARY OF THE INVENTION

One aspect of the present invention provides a skin treatment device comprising a plurality of electrodes applicable to a user's skin, wherein at least one of the electrodes at least partly encloses another at least one of the electrodes; at least one radio frequency (RF) generator, arranged to deliver RF energy to the skin via the electrodes; and a control unit arranged to control RF energy delivery by the at least one RF generator to the skin according to a specified transmission plan comprising controlling relative electrode polarities to concentrate the delivered RF energy to a specified skin volume below the skin surface.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1A:
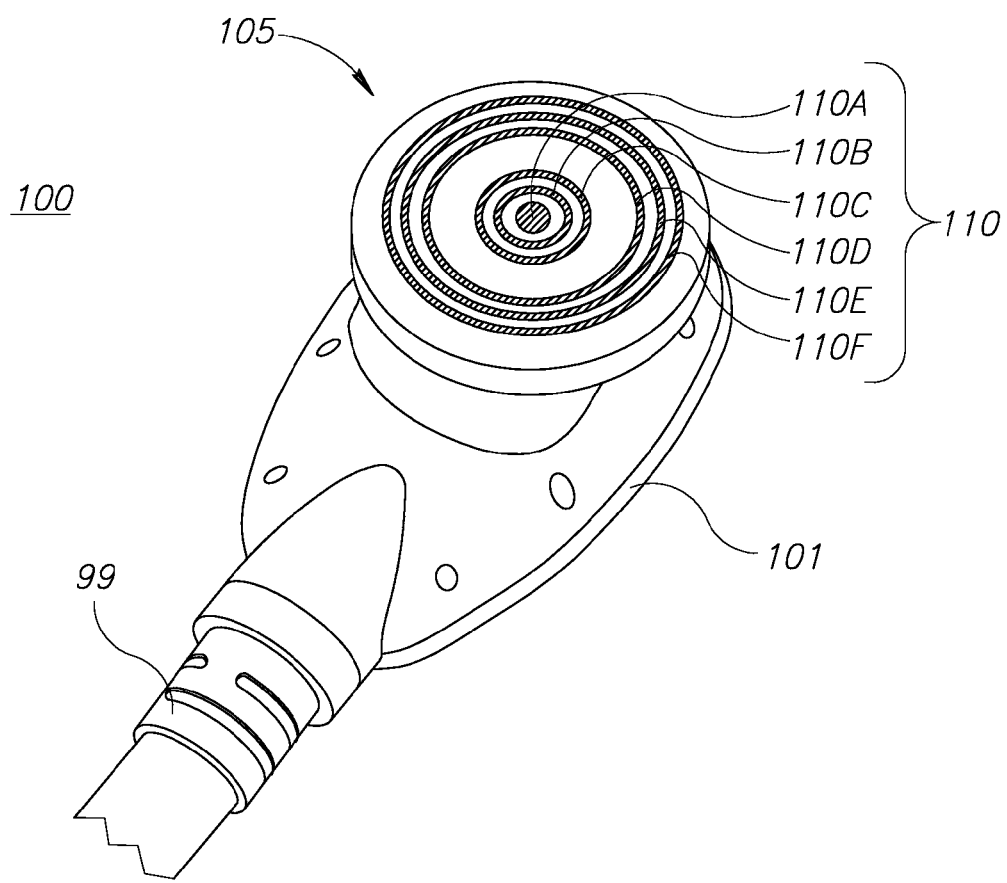
FIGS. 1A, 1B and 2 are high level schematic perspective illustrations of skin treatment devices, according to some embodiments of the invention.

Prior to the detailed description being set forth, it may be helpful to set forth definitions of certain terms that will be used hereinafter.

The term "skin treatment" as used herein in this application refers to any type of skin treatment such as skin heating, treating wrinkles or rhytides, treating skin aging by collagen remodeling, treating diseases of the skin such as acne and psoriasis, treating skin roughness, treating skin pigmentation, skin peeling, epidermal skin rejuvenation, reducing hyperhydrosis, reducing acne or providing any other therapeutic or cosmetic effect.

The term "RF energy" as used herein in this application refers to radiofrequency electromagnetic energy delivered by the electrodes to the skin as a result of electromagnetic potentials applied to the skin through the electrodes and causing currents to flow through and heat regions of the skin.

The term "phase" as used herein in this application refers to any value of the relative angle of a fluctuating current or voltage between electrodes which are driven from different RF sources. The terms "phase control" or "controlling the phase" of the delivered current or voltage, as used herein in this application, refer to setting a specific phase value to delivered current or voltage. The specific phase value may be any value from 0° to 360° (0 to 2 π radians). The term "relative phase" between electrodes, as used herein in this application, refers to any phase difference between electrodes, including a zero phase difference.

The term "polarity" as used herein in this application in relation to electrodes, refers to the electrode being a positive pole or a negative pole with respect to current delivery. The term "same polarity" as used herein in this application with reference to two electrodes, refers to the two electrodes having the same polarity during most of the time, i.e. the two electrodes being in the same polarity longer than they are in opposite polarities, or, using phase terms, have a phase difference between +90° and −90° (−π/2 to +π/2 radians). The signs + and − as used herein in this application to refer to electrode polarities schematically designate which electrodes have the same polarity, in the sense explained above. The phase between electrodes having the same sign may be zero but may also have any value between +90° and −90° (−π/2 to +π/2 radians). Different electrodes in the + or − groups may have different phase difference values between them. Some or all of the electrodes in each of the + or − groups may have a zero phase difference between them.

The term "potential barrier" as used herein in this application refers to an effect within the skin tissue volume of applying the same polarity as defined above to adjacent electrodes. As both adjacent electrodes induce similar charges into adjacent skin volumes, each of the charged skin volumes repels currents having a similar polarity from entering the skin volumes. Without wishing to be bound by theory, the repulsion effect of the potential barrier is used in the current invention to drive currents deeper into the skin volume and to control the depth through which currents flow. Potential barriers are schematically illustrated in FIGS. 5A-5E.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Radiofrequency (RF) skin treatment devices and methods are provided herein. RF energy is delivered via concentric electrodes in a phase-controlled manner which heats skin volumes below the surface more than the skin surface itself. The combination of controlling the phases of the RF energy delivered to different electrodes and the concentric configuration of the electrodes allows concentrating the delivered energy in specific regions below the skin surface at a particularly high efficiency. Configurations of the concentric electrodes, their forms and combinations with other electrodes and the phase polarities applied to the electrodes are also provided.

Figure 1B:
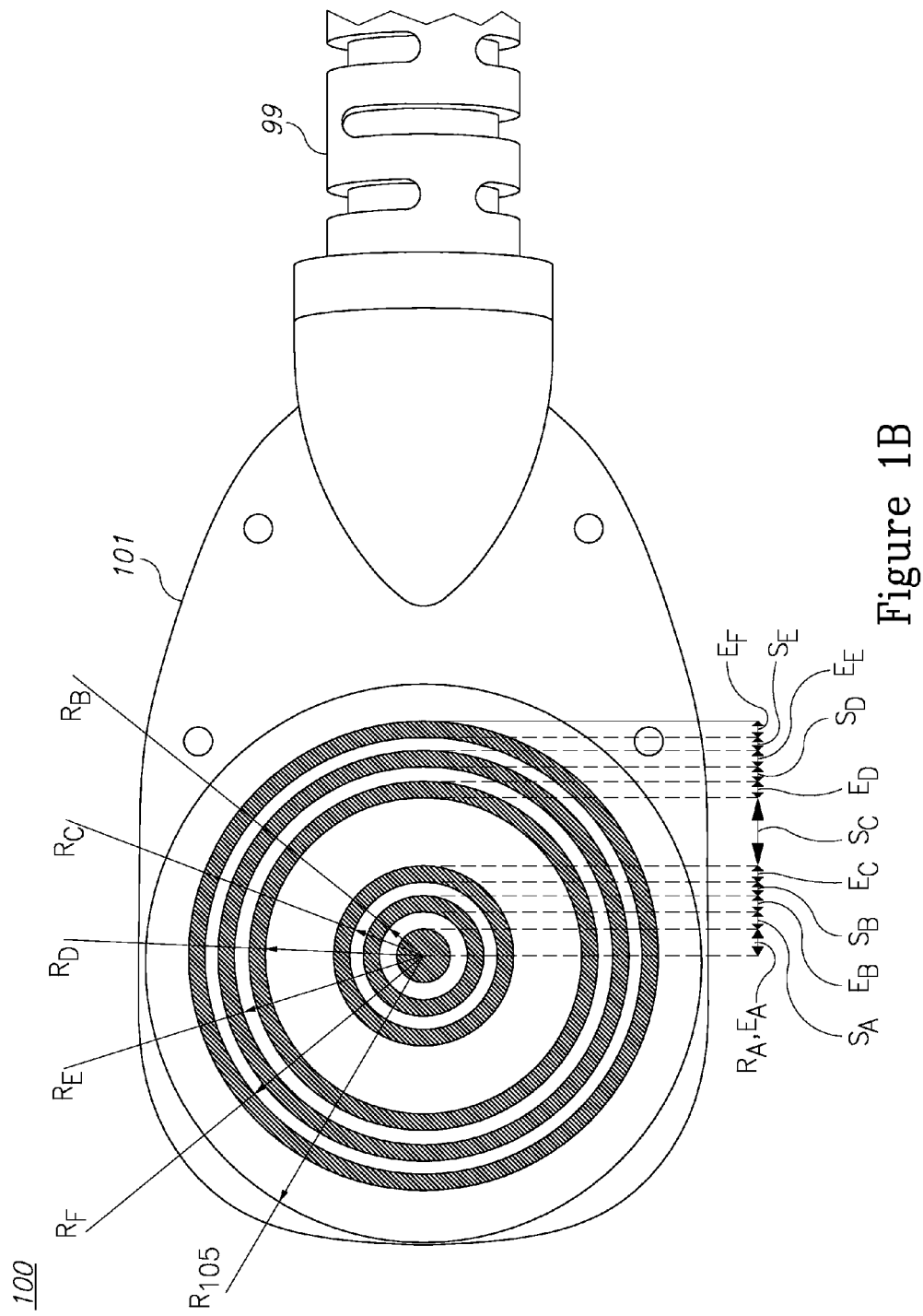
Figure 2:
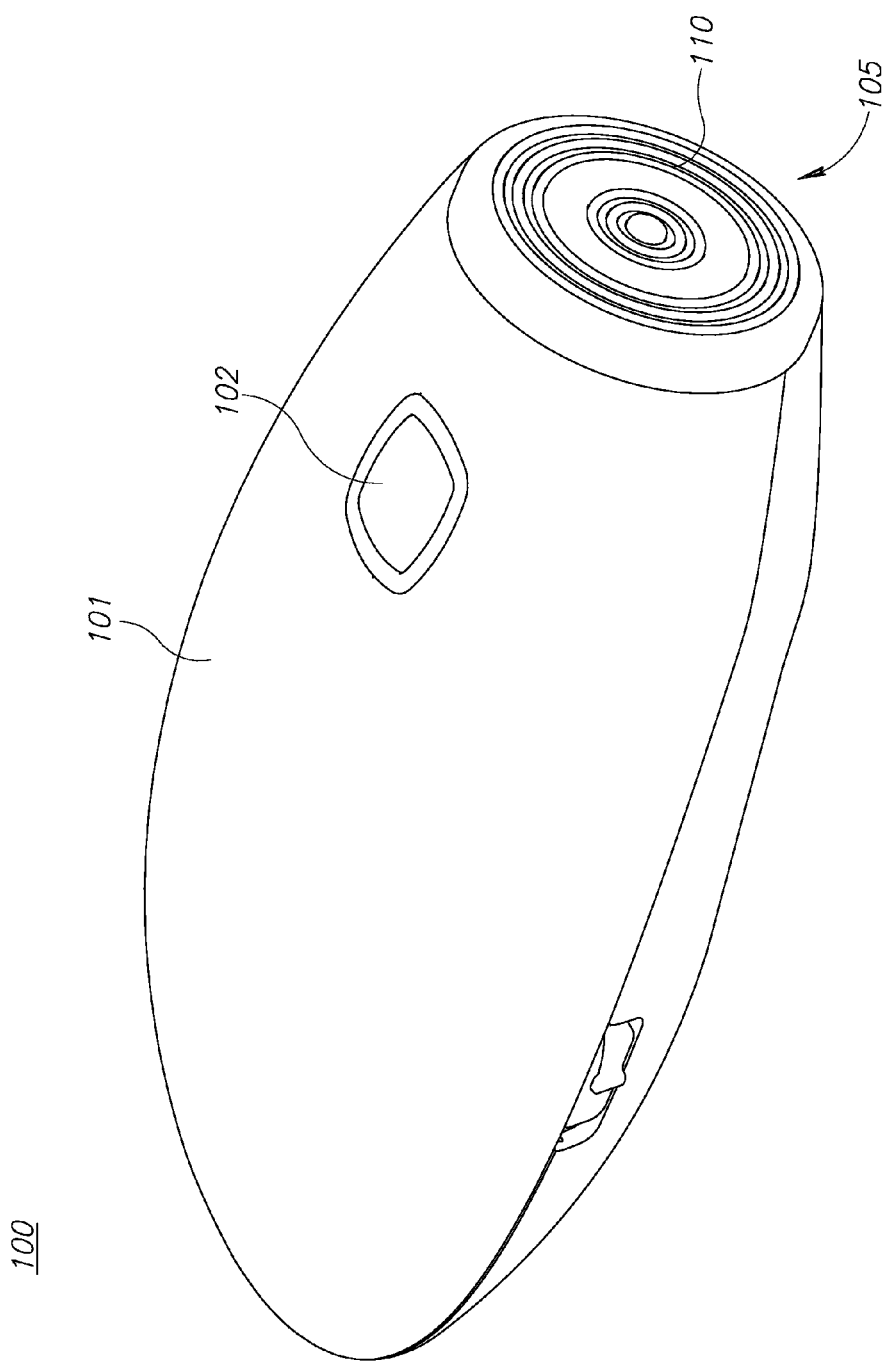

FIGS. 1A, 1B and 2 are high level schematic perspective illustrations of skin treatment devices 100 according to some embodiments of the invention. FIGS. 1A and 1B schematically illustrate device 100 connected via a cable 99 to a central unit, while FIG. 2 schematically illustrates device 100 as an independent unit having a power source (not shown) within a housing 101.

Skin treatment device 100 comprises a plurality of concentrically arranged electrodes 110 applicable to a user's skin, a radio frequency (RF) generator (not shown), arranged to deliver RF energy to the skin via electrodes 110; and a control unit (not shown) arranged to control RF energy delivery by the RF generator to the skin according to a specified transmission plan comprising controlling relative electrode polarities to concentrate the delivered RF energy to a specified skin volume below the skin surface. The specified transmission plan may be configured to keep a surface of the skin below a specified temperature threshold and/or to elevate a temperature of a specified skin volume below the surface of the skin (the elevated temperature being with respect to the surface of the skin).

Skin treatment device 100 comprises at least one of electrodes 110 at least partly encloses another at least one of electrodes 110. In certain embodiments, some electrodes 110 may be concentric, some electrodes may be eccentric with relation to each other. The degree to which certain electrodes 110 enclose other electrodes 110 may be varied according to the required form of potential barriers within the skin, required heating depth and other specifications of device 100.

Electrodes 110 may be round and an innermost electrode 110A may be a disc. Electrodes 110 may be equally spaced or electrode groups may be defined by larger spaces between some of electrodes 110. For example, Electrodes 110 may comprise an inner electrode group (e.g., 110A, 110B and 110C in FIG. 1A) which is interspaced from an outer electrode group (e.g., 110D, 110E and 110F in FIG. 1A). FIG. 1B schematically illustrates the following dimensional parameters of illustrated exemplary device 100. Electrodes 110A-110F are characterizes, respectively, by widths $E_A$, $E_B$, $E_C$, $E_D$, $E_E$ and $E_F$ and radii $R_A$, $R_B$, $R_C$, $R_D$, $R_E$ and $R_F$ (innermost disc-shaped electrode 110A is characterized by $E_A=R_A$), and are interspaced by spaces of widths $S_A$, $S_B$, $S_C$, $S_D$ and $S_E$. In the illustrated non-limiting case, inner group of electrodes 110A-C is separated from outer group of electrodes 110D-F by space $S_C$ of a larger width than the other inter-electrode spaces. $R_{105}$ denotes the radius of a face 105 of the applicator head, which clearly may have a shape other than circular as well and may at least partially be disposable.

Without wishing to be bound by theory, the spatial configuration and the phase configuration of electrodes 110 are understood to determine the heating pattern of the treated skin for given skin characteristics. In particular, as larger electric currents tend to flow through regions of lower impedance, controlling the phase and the polarity of electrodes 110 allows controlling the extent of tissue heating. For example, each of two adjacent electrodes having the same polarity (i.e., electrodes that are substantially in phase with each other) increases the impedance the other electrode experiences at the tissue region between the electrodes. Hence, pairs of electrodes with the same polarity create electrical potential barriers 113 (see FIGS. 5A-5E below) with increased impedance between the electrodes. Barriers 113 tend to drive the electric currents associated with the pair of electrodes deeper into the skin tissue (e.g., at an angle to the skin surface), as the increased impedance is experienced closer to the electrodes and hence closer to the surface. The specified transmission plan may be configured to assign electrode polarities to generate potential barrier 113 that drives the delivered RF energy to a specified skin volume below the surface of the skin.

Relative electrode polarities are controlled to deliver the RF energy preferentially below the surface of the skin, thus heating a skin volume below the surface to a greater extent than the skin surface is heated. The inventors have found out that using at least one electrode 110 that at least partly encloses at least one other electrode 110 intensifies the effect of the phase controlled energy delivery in the sense that more energy is delivered to the skin volume below the surface and less energy is delivered to the skin surface. Without being bound by theory, the inventors believe that the enclosing configuration of the electrodes prevents or reduces lateral (i.e., horizontal on the skin surface) RF energy delivery from electrodes 110, and hence reduces significantly surface heating. Instead, more RF energy is delivered vertically or at an angle below the surface and thus a larger portion of the delivered energy actually heats up the specified skin volume below the surface of the skin. A most symmetric configuration is of concentric electrodes 110.

Such a configuration may maximize the current concentration effect. However, the present invention is not limited to configurations with concentric electrodes and comprises partially concentric, eccentric, and varying degrees of enclosing by electrodes 110. Any of enclosing electrodes 110 and enclosed electrodes 110 may have different forms, such as round, circular, elliptic, partially circular, linear etc.

The relative electrode polarities may be determined according to specific purposes, requirements and configurations, and may be changed dynamically. For example, the relative electrode polarities may be controlled to yield one innermost electrode 110A with a reversed polarity with respect to outer electrodes 110B-F. In another example, the relative electrode polarities may be controlled to yield an inner electrode group (e.g., 110A, 110B and 110C in FIG. 1A) with a reversed polarity with respect to an outer electrode group (e.g., 110D, 110E and 110F in FIG. 1A). While the figures illustrate six electrodes, similar concentric configurations may be designed with any number of electrodes 110, in non-limiting examples, four or eight, but also larger numbers and odd numbers.

Housing 101 of device 100 may be arranged to hold electrodes 110 and electronic circuitry for operating electrodes 110. Housing 101 may be ergonomically designed, for example to apply the treatment in a paintbrush-like continuous manner. Housing 101 may comprise a mechanism that assures contact of electrodes 110 with the skin. Device 100 may be operated by pressing a button 102. Device 100 may be arranged to operate at different intensities by pressing button 102 at different patterns (repeatedly, continuously, etc.). The RF generator or generators may be external and connected via cable 99 or be internal in housing 101. Power supply may be inductive. The RF generator may be regulated by a RF voltage regulator and controlled by the control unit such as a micro controller, as described in detail in the parent applications. The control unit may be associated with a trigger and a low voltage regulator. The control unit may be further arranged to control the phase of each electrode 110A-F and to coordinate the polarities of the electrodes. Hence, the control unit may be arranged to set any specified phase between any two electrodes 110 to exactly control energy delivery to the skin. In particular, the control unit may designate reversed polarities to subgroups of electrodes 110. The reversed polarities may be approximate (i.e., not necessarily 180° but also, e.g., 120° or 160°, etc.) as explained above. The phase differences between electrodes 110 may be pre-determined and could be controlled during operation or be maintained constant at a predefined phase. The transmission plan may comprise controlling relative electrode polarities to concentrate the delivered RF energy to a specified skin volume. For example, the relative electrode polarities may be controlled to yield one or two pairs of adjacent electrodes 110 with substantially the same polarity. The control unit may be arranged to control the relative electrode polarities of the at least one partly enclosing electrode and of the at least one partly enclosed electrode to form a potential barrier around the latter within the specified skin volume.

Electrodes 110A-110F may all be connected via a transformer to a single generator or several generators may be used to supply the RF energy to electrodes 110. Paired electrode configurations (having the electrodes connected to both poles of the generator may be practical in home use devices to reduce the number of generators, while because commercial devices for use in professional clinic settings may have multiple grounded generators, each providing a single electrode. Some of electrodes 110A-110F may be connected together to improve current delivery and heating. Thus devices 100 having a specified number of generators may be used to deliver RF energy via a larger number of electrodes by interconnecting some of the electrodes to single generators.

In certain embodiments, the control unit may be further arranged to derive a realtime estimation of skin impedance and adjust the delivered energy according to the estimated skin impedance, resulting in more predictable results. The skin impedance estimation may be derived from measuring energy delivery with respect to applied voltage (skin impedance increases with the treated skin volume). Different energy delivery parameters may be applied to treating different skin region (e.g., in the face, the eye region is characterized by thin skin in the range of 1 mm, while the cheek region is characterized by thin skin in the range of 3-4 mm).

In certain embodiments, skin treatment with device 100 may be combined with any other treatment method, e.g. light or ultrasound delivery, application of gels, creams, topical formulations etc.

Certain embodiments may comprise central disc-shaped electrodes 110A having a diameter ($2 R_A$) between 4 mm and 12 mm and circular electrodes 110B-F each having a width ($E_B$, $E_C$, $E_D$, $E_E$ and $E_F$) between 1 mm and 3 mm. Adjacent electrodes may be spaced ($S_A$, $S_B$, $S_C$, $S_D$ and $S_E$) between 1 mm and 3 mm apart, and electrode groups may be interspaced between 3 mm and 6 mm apart ($S_C$ in the example illustrated in FIG. 1B). Thus, electrode radii may span a range between 1-4 mm for innermost electrode 110A ($R_A$) to 80 mm for outermost electrode 110F ($R_F$), other electrodes 110B-E having intermediate radii. In certain embodiments, the areas of electrodes 110A-F may range between 0.1 mm$^2$ and 10 cm$^2$, depending on the selected widths and radii.

In certain embodiments, skin treatment device 100 may comprise at least one of electrodes 110 which is made of plastic (e.g., polycarbonate plastic) coated by a conductive coating. At least a part of device 100, e.g., at least part of face 105 of the applicator head containing at least one of electrodes 110, may be configured to be detachable and disposable. Face 105 of device 100 which hold electrodes 110 may be flat or slightly curved and may comprise surface features.

Figures 3A, 3B:
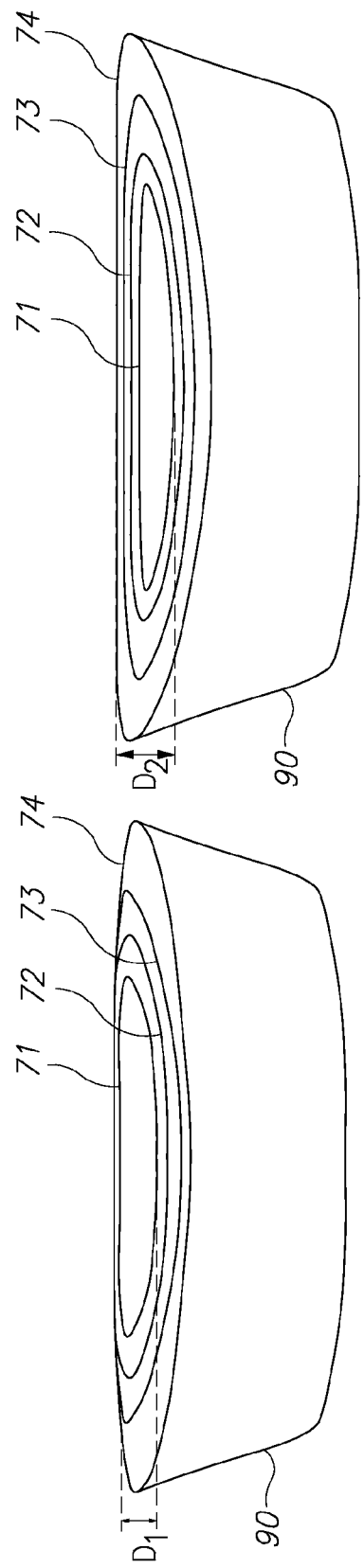
FIGS. 3A, 3B, 4A and 4B schematically illustrate experimental results of applying skin treatment devices onto gel material that simulates the skin.
Figure 4B:
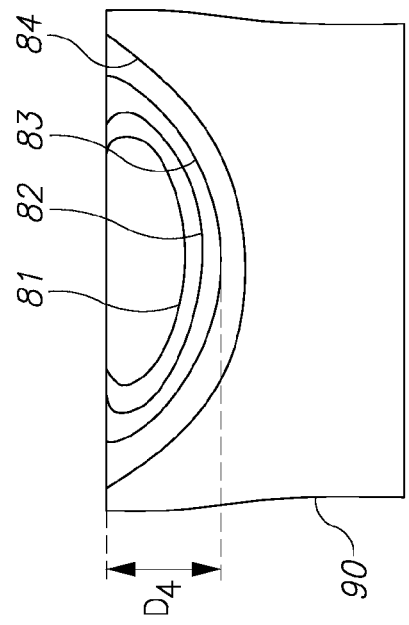
Figure 4A:
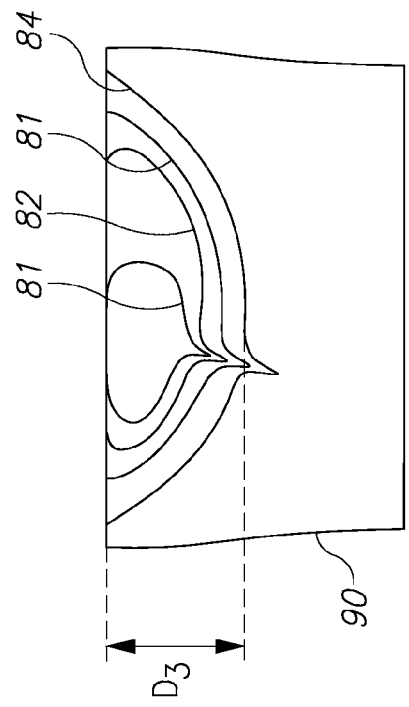

FIGS. 3A, 3B, 4A and 4B schematically illustrate experimental results of applying skin treatment device onto gel material that simulates the skin. FIGS. 3A and 4A illustrate application of RF devices having linearly arranged electrodes (similar to devices described in the parent applications, while FIGS. 3B and 4B illustrate devices 100, according to some embodiments of the invention. The illustrations are tracings of lines 71-74 and 81-84 respectively, which mark regions with equal temperature, upon application of skin treatment devices. FIGS. 3A and 3B illustrate a case of a dynamic treatment in which the respective device is moved during treatment, while FIGS. 4A and 4B illustrate a case of a static treatment in which the respective device is not moved during the treatment. In all four figures the devices applied a power of 40 Watts.

In FIGS. 3A and 3B, lines 71, 72, 73 and 74 mark temperatures of approximately 35° C., 31° C., 26° C. and 21° C., respectively, for dynamic device application for four minutes. The depths $D_1$ and $D_2$ denote, respectively, the depth in the material over which a temperature difference of 15° C. was created. While the prior art device with linearly arranged electrodes yielded $D_1$=3.65 mm, device 100 with concentric electrodes yielded $D_2$=8.80 mm, i.e., a more effective heating below the skin's surface. FIGS. 3A and 3B also illustrate that the skin surface is above the temperature line of 26° C., i.e., the temperature of the skin volume below the surface is elevated with respect to the temperature of the skin surface by over 9° C. Due to the dynamic application the heated skin volume below the surface has a much larger horizontal extent than vertical extent.

In FIGS. 4A and 4B, lines 81, 82, 83 and 84 mark temperatures of approximately 44° C., 35° C., 31° C. and 26° C., respectively, for static device application for half a minute. The static application allows temperature differences to build up, and thus temperatures are higher and heated regions are larger. It is noted that actual application on the skin is recommended to be dynamic, and the illustrated static application is presented mainly for illustrative purposes. In the illustrated example, heating depths $D_3$, $D_4$ are similar in the prior art device and in device 100 (FIGS. 4A and 4B respectively), namely ca. 10 mm for a 25° C. temperature difference, ca. 12 mm for a 20° C. temperature difference and ca. 14 mm for a 15° C. temperature difference. However, device 100 provides a larger and more uniform heated volume than the prior art device as seen in the extent of the region with temperature larger than 44° C. (device 100 in FIG. 4B heats about double the volume heated by the prior art device illustrated in FIG. 4A) and in the 35° C., 31° C. and 26° C., which are strongly curved using the linearly arranged electrodes (FIG. 4A) but smooth and gradual using device 100 (FIG. 4B).

Figure 5A:
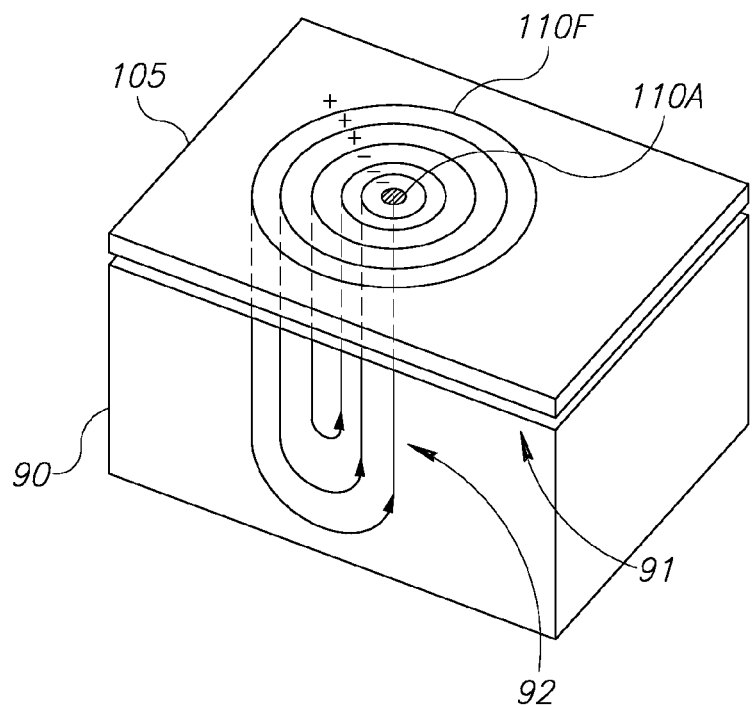
FIGS. 5A-5G are high level schematic perspective illustrations of skin volume heating by controlling electrode polarities, according to some embodiments of the invention.
Figure 5B:
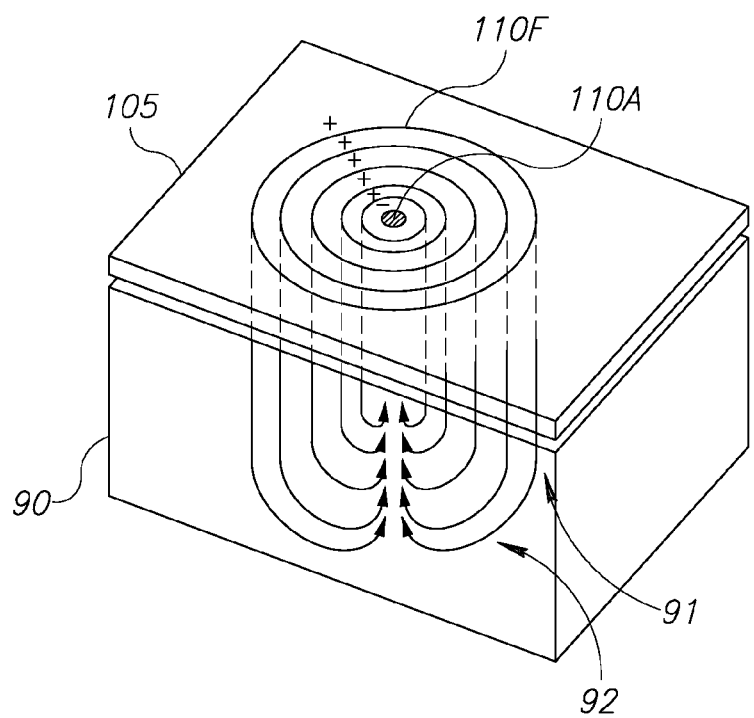
Figure 5C:
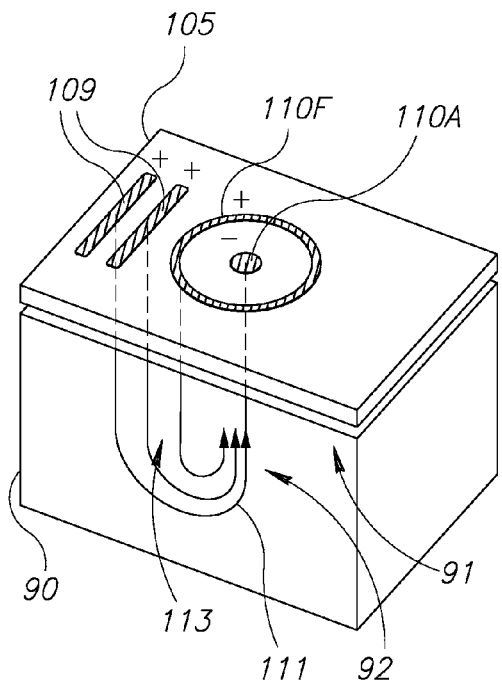

FIGS. 5A-5E are high level schematic perspective illustrations of skin volume heating by controlling electrode polarities, according to some embodiments of the invention. Electrode configurations which are illustrated in FIGS. 5A-5C are non-limiting examples, and other electrode configurations, derived from the principles described below are likewise within the scope of the invention. FIGS. 5A-5C schematically illustrate face 105 of the applicator head of device 100 which hold electrodes 110, placed upon a user's skin 90. The head is applied onto surface 91 of skin and produces a heating of skin tissue volume 92 below surface 91. Device 100 is configured, through the configuration of the phase polarities of different electrodes 110, to heat skin volume 92 and elevate its temperature beyond the temperature of skin surface 91.

FIGS. 5A and 5B schematically illustrate device 100 having innermost disc-shaped electrodes 110A and ring-shaped electrodes 110B-F (similar to FIG. 1A), concentrically arranged with respect to innermost electrode 110A. FIGS. 5A and 5B, as well as FIGS. 5C-5E below, further illustrate schematically electrode polarities by "+" and "−" signs, denoting that the respective electrodes are allocated reverse polarities. It is noted that the term "reverse polarities" refers to electrodes having differing polarities during most of the time, i.e., having reversed phase polarities longer than they have similar polarities, or, using phase terms, having a phase difference larger than +90° or smaller than −90° (>+π/2 or <−π/2 radians). Different electrodes in the "+" or "−" groups may have different phase difference values between them (but within −π/2 to +π/2 within each group). Some or all of the electrodes in each polarity group may have a zero phase difference between them.

Finally, FIGS. 5A-5E schematically illustrate resulting currents 111 within skin volume 92. While varying the specific electrode configuration changes the specific current patterns within skin 90, devices 100 are arranged to configure electrode polarities to form at least one barrier 113 which drives currents 111 deeper than skin surface 91 and into skin tissue volume 92. Any of electrodes 110A-110F as well as resulting barriers 113 may be circular, semi-circular or circular with missing sectors. Without being bound by theory, any of electrodes 110B-110F may be shaped to shield inner electrodes from receiving surface currents from external electrodes having a reversed polarity, thus forcing currents 111 to penetrate skin volume 92 below skin surface 91.

FIG. 5A schematically illustrates an inner group of electrodes 110A-110C which has a reversed polarity with respect to an outer group of electrodes 110D-110F (see FIG. 1A for full electrode reference numerals). In this case, barrier 113 is formed as a cylindrical skin volume below the space that separates the inner group from the outer group. As barrier 113 is circular, no surface current is allowed to flow between inner group electrodes 110A-110C and outer group electrodes 110D-110F. Thus, more current flows into the depth of the skin tissue, resulting in a larger temperature difference between skin volume 92 below the surface and skin surface 91 itself.

FIG. 5B schematically illustrates innermost electrodes 110A which has a reversed polarity with respect to the other electrodes 110B-110F. In this case, barrier 113 is formed as a cylindrical skin volume below the space that separates innermost electrode 110A from other electrodes 110B-110F (see FIG. 1A for full electrode reference numerals). As barrier 113 is circular, no surface current is allowed to flow between innermost electrode 110A and outer electrodes 110B-110F. Thus, more current flows into the depth of the skin tissue, resulting in a larger temperature difference between skin volume 92 below the surface and skin surface 91 itself. The inventors have found out in this case that heating power is increased by ca. 30% with respect to linearly arranged linear electrodes with controlled phase transmission. Certain embodiments enable using 85-90% of the delivered energy to heat skin volume 92 below skin surface 91 with little of the delivered energy heating skin surface 91. Certain embodiments comprise a bipolar arrangement of electrodes 110, in which electrodes 110 are arranged in pairs of reversed polarities, which is configured to heat skin surface 91. Device may allow switching between a phase-controlled mode and a bipolar mode of operation.

FIG. 5C schematically illustrates device 100 having inner disc-shaped electrode 110A, outer ring-shaped electrode 110F, concentrically arranged with respect to inner electrode 110A, as well as adjacent linear electrodes 109. Clearly, several concentric electrodes 110 may be positioned between inner and outer electrodes 110A, 110F, respectively, and linear electrodes 109 may vary in number and be positioned at different locations around outer electrode 110F. As illustrates schematically in FIG. 5C, outer electrode 110F shields inner electrode 110A from linear electrodes 109 and forms potential barrier 113 within skin volume 92 which drives currents 111 into the depth of the skin tissue, heating hence skin volume 92 more than skin surface 91.

Figure 5D:
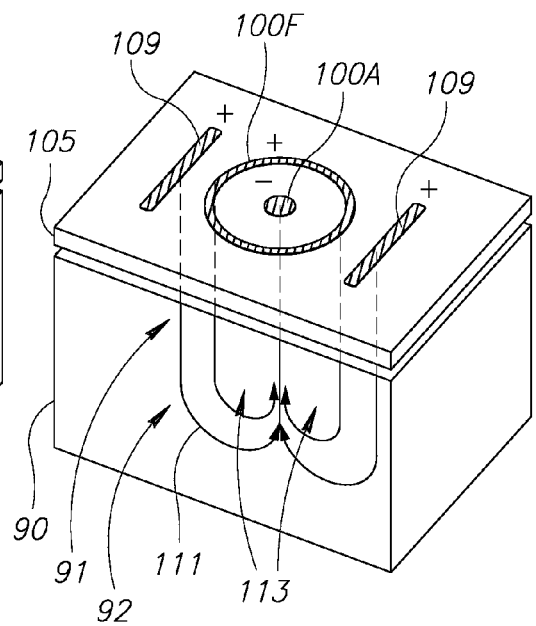

FIG. 5D schematically illustrates device 100 having inner disc-shaped electrode 110A, outer ring-shaped electrode 110F, concentrically arranged with respect to inner electrode 110A, as well as adjacent linear electrodes 109 at either side of outer electrode 110F. Clearly, several concentric electrodes 110 may be positioned between inner and outer electrodes 110A, 110F, respectively, and linear electrodes 109 may vary in number and be positioned at different locations around outer electrode 110F. As illustrates schematically in FIG. 5D, outer electrode 110F shields inner electrode 110A from linear electrodes 109 on either side thereof, and forms potential barrier 113 within skin volume 92 which drives currents 111 into the depth of the skin tissue, heating hence skin volume 92 more than skin surface 91.

Figure 5E:
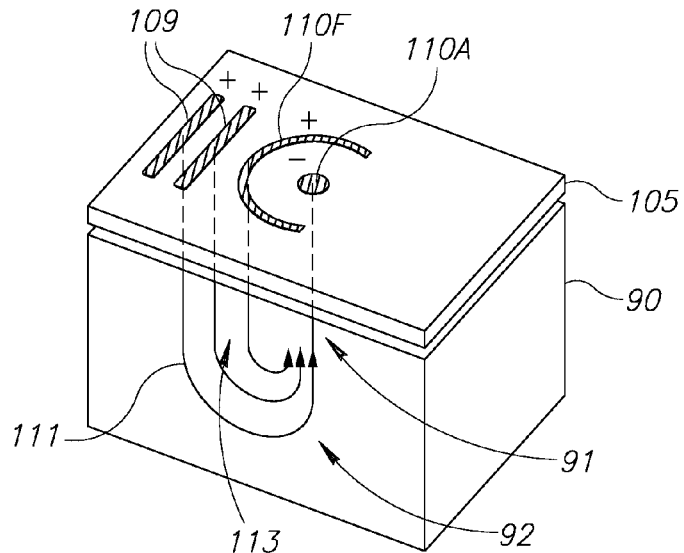

FIG. 5E schematically illustrates device 100 having inner disc-shaped electrode 110A, outer electrode 110F, concentrically arranged with respect to inner electrode 110A, as well as adjacent linear electrodes 109. Outer electrode 110F may be a semi-circle, or be shaped as a ring which lacks a sector, to shield inner electrode 110A from linear electrodes 109 in their respective direction. The missing sector of outer electrode 109 may not reduce the strength of barrier 113 significantly, as no electrodes of reversed polarity (with respect to innermost electrode 110A) are positioned near the missing sector. Clearly, several concentric electrodes 110 may be positioned between inner and outer electrodes 110A, 110F, respectively, and linear electrodes 109 may vary in number and be positioned at different locations around outer electrode 110F. As illustrates schematically in FIG. 5D, outer electrode 110F shields inner electrode 110A from linear electrodes 109 and forms potential barrier 113 within skin volume 92 which drives currents 111 into the depth of the skin tissue, heating hence skin volume 92 more than skin surface 91.

Skin treatment device 100 may hence comprise a plurality of electrodes 110 applicable to user's skin 90, wherein at least two of electrodes 110 are concentric. At least one of electrodes 110 may be linear (indicated as linear electrodes 109), at least one of electrodes 110 may be ring-shaped and/or at least one of electrodes 110 may be shaped as a ring that lacks a sector. All or some of electrodes 110 may be concentric and/or the at least two concentric electrodes may be round.

Figure 5F:
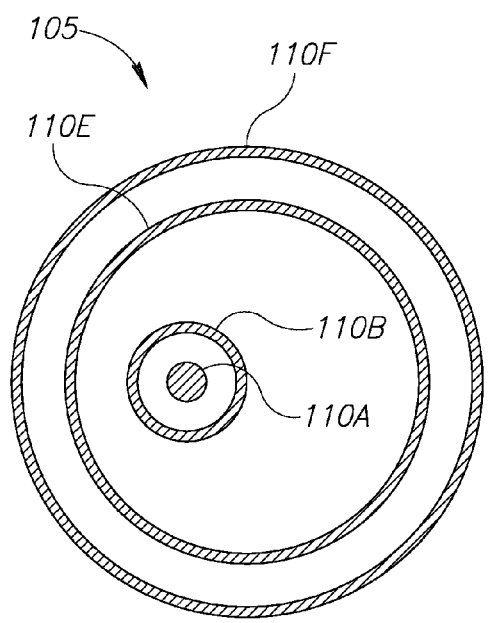
Figure 5G:
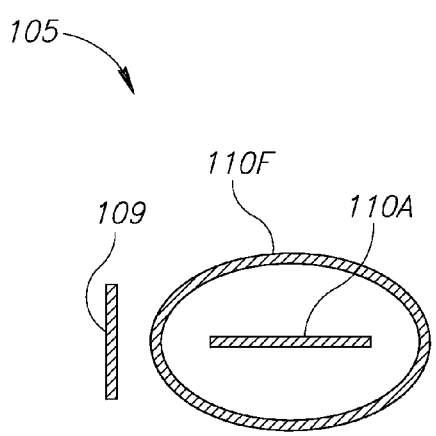

FIGS. 5F and 5G schematically illustrate additional electrode configuration principles, according to some embodiments of the invention. FIG. 5F schematically illustrates concentric electrodes 110E, 110F enclosing, in an eccentric manner, concentric electrodes 110A, 110B. Any relative positioning of electrodes 110 may be designed to achieve required heating effects. FIG. 5G schematically illustrates a combination of electrodes including outer elliptic electrode 110F enclosing innermost linear electrode 110A which is perpendicularly positioned with respect to outer linear electrode 109. Elements from the configuration illustrated in FIG. 5G may be applied to any of the other illustrated configurations, for example elliptic electrodes, linear electrode at different angles and linear innermost electrodes.

Any of the electrode configurations describes above may be modified according to other configurations, e.g., any of electrodes 110 may be positioned eccentrically or be made to partly enclose inner electrodes 110, as illustrated in FIG. 5E, all with respect to specific requirements.

The configurations presented above are non-limiting examples for configurations with four and six electrodes. They are not to be taken as limiting the number of electrodes but as indicating plausible configurations of larger numbers of electrodes.

In embodiments, the control unit may be further arranged to derive a realtime estimation of skin impedance and adjust the delivered energy according to the estimated skin impedance, resulting in more predictable results. The skin impedance estimation may be derived from measuring energy delivery with respect to applied voltage (skin impedance increases with the treated skin volume). Different energy delivery parameters may be applied to treating different skin region (e.g., in the face, the eye region is characterized by thin skin in the range of 1 mm, while the cheek region is characterized by thin skin in the range of 3-4 mm).

Figure 6:
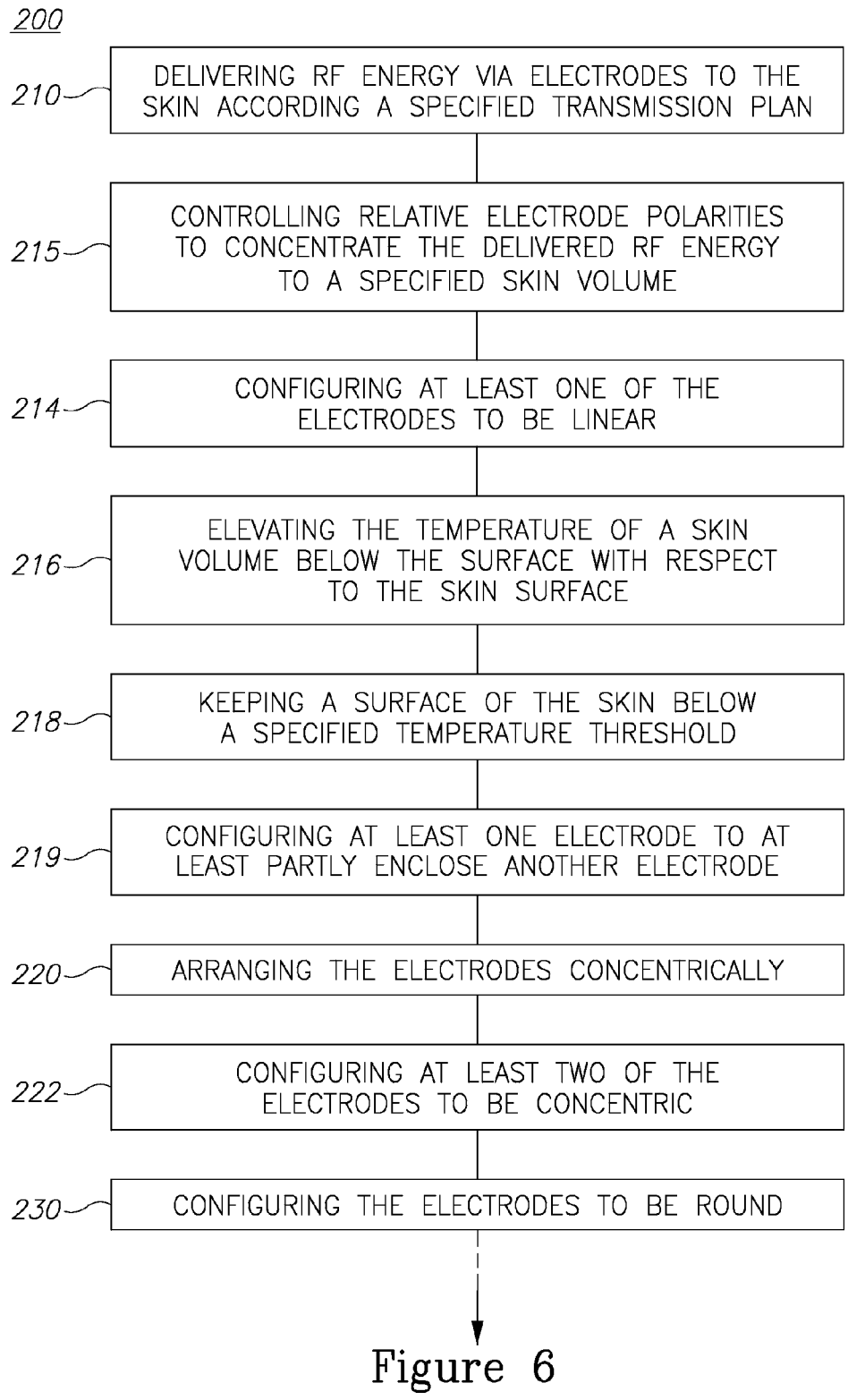
FIG. 6 is a high level schematic flowchart illustrating a skin treatment method, according to some embodiments of the invention.

FIG. 6 is a high level schematic flowchart illustrating methods 200 according to some embodiments of the invention. Methods 200 comprise methods of configuring RF skin treatment applicator heads and skin treatment methods.

Method 200 may comprise delivering RF energy via electrodes to the skin according a specified transmission plan (stage 210), arranging the electrodes concentrically (stage 220) and controlling relative electrode polarities to concentrate the delivered RF energy to a specified skin volume (stage 215).

Method 200 may comprise designing the transmission plan to maximize the RF energy delivery below a subgroup of the electrodes (stage 212) and/or elevating the temperature of a skin volume below the surface with respect to the skin surface (stage 216) and/or keeping a surface of the skin below a specified temperature threshold (stage 218). In certain embodiments, method 200 may comprise configuring at least one electrode to at least partly enclose another electrode (stage 219).

Method 200 may comprise configuring at least two of the electrodes to be concentric (stage 222), configuring the electrodes to be round (stage 230), configuring at least one of the electrodes to be linear (stage 214), using at least one electrode which is shaped as a ring that lacks a sector (stage 232) and/or using an innermost disc-shaped electrode (stage 235).

Method 200 may comprise applying reverse polarities to the innermost electrode with respect to outer electrodes (stage 240) or applying reverse polarities to an inner group of electrodes with respect to an outer group of electrodes (stage 245). Method 200 may comprise assigning electrode polarities to generate a potential barrier that drives current to skin volume below the skin surface (stage 247). Method 200 may comprise enclosing at least one electrode by another electrode which is supplied with a reversed polarity to generate the potential barrier (stage 248). Method 200 may further comprise interspacing the inner and outer electrode groups with reverse polarity (stage 249).

Method 200 may comprise using plastic electrodes covered by a conductive coating (stage 250) and/or configuring at least part of the applicator head to be disposable (stage 252).

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Embodiments of the invention may include features from different embodiments disclosed above, and embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A skin treatment device comprising:
a plurality of electrodes configured to directly contact a skin surface of a user's skin non-invasively, wherein at least one of the electrodes at least partly encloses another at least one of the electrodes;
a plurality of radio frequency (RF) generators, arranged to deliver RF energy to the skin via the electrodes, wherein the at least one of the electrodes and the another at least one of the electrodes enclosed thereby—are connected to different RF generators; and
a control unit arranged to control RF energy delivery by the RF generators through the electrodes to the skin according to a specified transmission plan comprising controlling relative phases between the RF generators and relative electrode polarities to yield at least one pair of adjacent electrodes with the same polarity to concentrate the delivered RF energy to a specified skin volume at a predetermined depth below the skin surface,
wherein the specified transmission plan is configured to elevate a temperature of the specified skin volume with respect to the skin surface while keeping the skin surface below a specified temperature threshold.

2. The skin treatment device of claim 1, wherein the control unit is arranged to control the relative electrode polarities of the at least one partly enclosing electrode and of the at least one partly enclosed electrode to form a potential barrier around the latter within the specified skin volume.

3. The skin treatment device of claim 1, wherein at least one of the electrodes is at least one of: linear, ring-shaped or shaped as a ring that lacks a sector.

4. The skin treatment device of claim 1, wherein the relative electrode polarities are controlled to yield one electrode with a reversed polarity with respect to the other electrodes; or to yield one innermost electrode with a reversed polarity with respect to at least one outer electrode.

5. The skin treatment device of claim 1, wherein the relative electrode polarities are controlled to yield one electrode group with a reversed polarity with respect to another electrode group; or to yield an inner electrode group of electrodes with a reversed polarity with respect to an outer electrode group of electrodes, wherein each of the inner and outer groups comprises at least one electrode.

6. The skin treatment device of claim 1, wherein the electrodes comprise an inner electrode group which is interspaced from an outer electrode group, wherein each of the inner and outer groups comprises at least one electrode.

7. The skin treatment device of claim 1, wherein at least two or all of the electrodes are concentric and round, and an innermost electrode is a disc.

8. The skin treatment device of claim 1, wherein the specified transmission plan is configured to assign electrode polarities to generate a potential barrier that drives the delivered RF energy to a specified skin volume below the surface of the skin.

9. The skin treatment device of claim 1, wherein at least one of the electrodes is made of plastic coated by a conductive coating.

10. The skin treatment device of claim 1, wherein at least a part of the device, containing at least one of the electrodes, is configured to be disposable.

11. A method comprising:
configuring an RF skin treatment applicator head by arranging at least one electrode to at least partly enclose another electrode on the head, wherein the enclosing and the enclosed electrodes are connected to different RF generators, and wherein the electrodes are configured to directly contact a skin surface of a user's skin non-invasively, and
controlling polarities of at least two adjacent electrodes connected to different RF generators by controlling relative phases between the RF generators, to be the same polarity to elevate a temperature of a specified skin volume with respect to the skin surface.

12. The method of claim 11, further comprising arranging at least two or all electrodes to be concentric.

13. The method of claim 11, further comprising arranging at least two electrodes into an inner group and an outer group, wherein each of the inner and outer groups comprises at least one electrode.

14. The method of claim 13, further comprising configuring at least one of the electrodes to be at least one of: disc-shaped, round, circular, and shaped as a ring that lacks a sector.

15. A skin treatment method comprising:
configuring a plurality of electrodes to comprise at least one of the electrodes at least partly enclosing another at least one of the electrodes, wherein the enclosing and the enclosed electrodes are connected to different RF generators, and wherein the electrodes are configured to directly contact a skin surface of a user's skin non-invasively, and
delivering RF energy, by multiple RF generators, via the plurality of electrodes to a user's skin according to a specified transmission plan, the specified transmission plan comprising controlling relative phases between the RF generators and relative electrode polarities to yield at least one pair of adjacent electrodes with the same polarity to concentrate the delivered RF energy to a specified skin volume,
wherein the specified transmission plan is configured to elevate a temperature of the specified skin volume with respect to the skin surface while keeping the skin surface below a specified temperature threshold.

16. The skin treatment method of claim 15, further comprising configuring the specified transmission plan to keep a surface of the skin below a specified temperature threshold and elevating, by the delivered RF energy, a temperature of the specified skin volume below the surface with respect to the skin surface.

17. The skin treatment method of claim 15, further comprising applying reverse polarities to at least an innermost electrode with respect to at least one other electrode.

18. The skin treatment method of claim 15, further comprising controlling relative electrode polarities of the at least one partly enclosing electrode and of the at least one partly enclosed electrode to form a potential barrier around the latter within the specified skin volume.

* * * * *